United States Patent
Kakushima et al.

(10) Patent No.: US 10,964,836 B2
(45) Date of Patent: Mar. 30, 2021

(54) PHOTON COUNTING-TYPE RADIATION DETECTOR AND RADIOLOGICAL INSPECTION DEVICE USING SAME

(71) Applicants: KABUSHIKI KAISHA TOSHIBA, Tokyo (JP); TOSHIBA MATERIALS CO., LTD, Kanagawa (JP)

(72) Inventors: Kuniyuki Kakushima, Kanagawa (JP); Tomoyuki Suzuki, Tokyo (JP); Kazuo Tsutsui, Kanagawa (JP); Akito Sasaki, Kanagawa (JP); Atsuya Sasaki, Kanagawa (JP); Hideaki Hirabayashi, Kanagawa (JP); Yoshinori Kataoka, Kanagawa (JP)

(73) Assignees: KABUSHIKI KAISHA TOSHIBA, Tokyo (JP); TOSHIBA MATERIALS CO., LTD, Yokohama (JP)

( * ) Notice: Subject to any disclaimer, the term of this patent is extended or adjusted under 35 U.S.C. 154(b) by 0 days.

(21) Appl. No.: 16/600,351

(22) Filed: Oct. 11, 2019

(65) Prior Publication Data
US 2020/0041663 A1 Feb. 6, 2020

Related U.S. Application Data

(63) Continuation of application No. PCT/JP2018/018371, filed on May 11, 2018.

(30) Foreign Application Priority Data

May 12, 2017 (JP) .............................. JP2017-095665

(51) Int. Cl.
*H01L 31/108* (2006.01)
*G01T 1/24* (2006.01)
*H01L 31/115* (2006.01)
*H01L 31/0312* (2006.01)
*G01N 23/083* (2018.01)
(Continued)

(52) U.S. Cl.
CPC ............ *H01L 31/108* (2013.01); *G01T 1/242* (2013.01); *H01L 31/0312* (2013.01); *H01L 31/115* (2013.01); *A61B 6/4241* (2013.01); *G01N 23/046* (2013.01); *G01N 23/083* (2013.01)

(58) Field of Classification Search
CPC . H01L 31/108; H01L 31/0312; H01L 31/115; G01T 1/242; G01N 23/046; G01N 23/083; A61B 6/4241
See application file for complete search history.

(56) References Cited

U.S. PATENT DOCUMENTS

2006/0056581 A1 3/2006 Hoffman
2007/0206721 A1 9/2007 Tkaczyk
(Continued)

FOREIGN PATENT DOCUMENTS

EP 0380340 A2 8/1990
JP S46-005177 A 11/1971
(Continued)

*Primary Examiner* — Michael C Bryant
(74) *Attorney, Agent, or Firm* — Foley & Lardner LLP

(57) ABSTRACT

According to one embodiment, a photon counting-type radiation detector includes a first cell and a second cell. The first cell transmits radiation. The second cell is stacked with the first cell. The second cell absorbs the radiation passing through the first cell.

18 Claims, 13 Drawing Sheets

(51) Int. Cl.
*A61B 6/00* (2006.01)
*G01N 23/046* (2018.01)

(56) References Cited

U.S. PATENT DOCUMENTS

| | | | |
|---|---|---|---|
| 2011/0058649 A1* | 3/2011 | Wear | A61B 6/4042 |
| | | | 378/55 |
| 2012/0175584 A1 | 7/2012 | Weinberg | |
| 2014/0346531 A1 | 11/2014 | Imai | |
| 2015/0287221 A1 | 10/2015 | Takayama | |
| 2015/0323685 A1* | 11/2015 | Nelson | G01T 1/1614 |
| | | | 250/370.08 |
| 2016/0206255 A1* | 7/2016 | Gagnon | A61B 6/4275 |
| 2017/0112457 A1 | 4/2017 | Allinson | |
| 2018/0059263 A1* | 3/2018 | Kameshiro | H01L 31/117 |

FOREIGN PATENT DOCUMENTS

| | | |
|---|---|---|
| JP | H2-264475 A | 10/1990 |
| JP | 2009-18154 A | 1/2009 |
| JP | 2011-56257 A | 3/2011 |
| JP | 4886151 B2 | 2/2012 |
| JP | 2014-128456 A | 7/2014 |
| JP | 2014-145705 A | 8/2014 |
| WO | WO-2016/143156 A1 | 9/2016 |

\* cited by examiner

PHOTON COUNTING-TYPE RADIATION DETECTOR AND RADIOLOGICAL INSPECTION DEVICE USING SAME

CROSS-REFERENCE TO RELATED APPLICATIONS

This is a continuation application of International Application PCT/JP2018/018371, filed on May 11, 2018. This application also claims priority to Japanese Patent Application No. 2017-095665, filed on May 12, 2017. The entire contents of each are incorporated herein by reference.

FIELD

An embodiment generally relates to a photon counting-type radiation detector and a radiological inspection device using the photon counting-type radiation detector.

BACKGROUND

Radiological inspection devices are used in various fields from medical devices to industrial non-destructive inspection devices and the like. A CT (Computed Tomography) device and a positron emission tomography (PET: positron emission Tomography) device are examples of medical devices. X-rays, gamma rays, and the like are used as the radiation.

As shown in Japanese Patent No. 4886151 (Patent Literature 1), generally, a light-emitting substance called a solid scintillator is used in an X-ray CT device. The solid scintillator is a substance that emits light by X-rays being irradiated. The X-ray CT device that uses the solid scintillator converts, into visible light, the X-rays passing through a screening object by using the solid scintillator. A tomogram is obtained by a photodiode detector changing the visible light into an electrical signal. Currently, by such a technique, it is also possible to obtain a three-dimensional image. On the other hand, a method of detecting the light emission of the solid scintillator as an electrical signal has a loss when changing the X-rays into light. Additionally, the reduction of the exposure amount of X-rays has been limited because the improvement of the light sensitivity of photodiodes is limited. Also, the downsizing of the solid scintillator has been limited because the solid scintillator is a polycrystalline body. Accordingly, the improvement of the spatial resolution has been limited. Furthermore, a technique of changing only the light emission of the solid scintillator into an electrical signal has the problem of a low X-ray information amount.

In recent years, a radiation detector is being developed in which the radiation passing through the screening object is converted directly into an electrical signal. A radiation detector in which a photon counting-type radiation detector is mounted is discussed in JP-A 2014-128456 (Kokai) (Patent Literature 2). The photon counting technique can convert the X-ray photons passing through the screening object directly into an electrical signal. Thereby, there are expectations for effects such as reducing the exposure amount, etc.

DETAILED DESCRIPTION

A photon counting-type radiation detector according to an embodiment includes a first cell and a second cell and has the following features. The first cell transmits X-rays. The second cell absorbs the radiation passing through the first cell. The second cell is stacked with the first cell.

Figure 1:
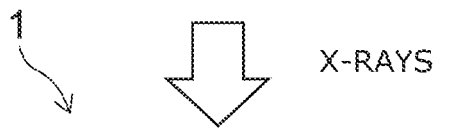
FIG. 1 is a schematic view showing an example of a photon counting-type radiation detector according to an embodiment.
Figure 2:
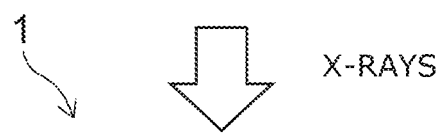
FIG. 2 is a schematic view showing another example of the photon counting-type radiation detector according to the embodiment.
Figure 3:
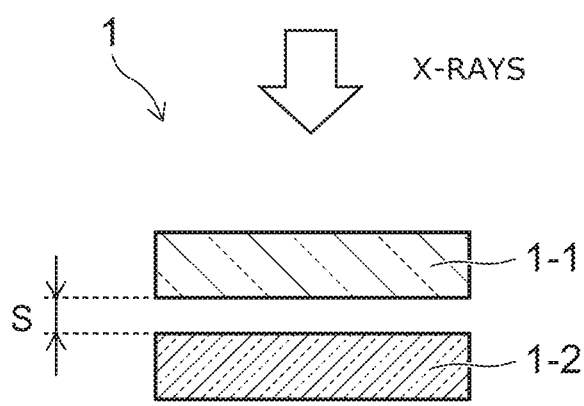
FIG. 3 is a schematic view showing yet another example of the photon counting-type radiation detector according to the embodiment.

FIG. 1 and FIG. 2 are schematic views showing examples of a photon counting-type radiation detector. In FIG. 1 and FIG. 2, 1 is a photon counting-type radiation detector. 1-1 is a first cell. 1-2 is a second cell. In FIG. 2, 1-3 is a third cell. FIG. 1 shows a two-layer stacked structure. FIG. 2 shows a three-layer stacked structure.

X-rays or gamma rays are examples of the radiation. A detector that uses X-rays is described below as an example.

X-rays that are generated from an X-ray generation source such as an X-ray tube, etc., pass through a screening object and reach the photon counting-type radiation detector. First, X-ray photons of the incident X-rays are detected by the first cell. At this time, the X-rays pass through the first cell. The X-rays that pass through the first cell reach the second cell. In the case where the stacked structure is made of two layers, the X-ray photons of the X-rays passing through the screening object can be detected by both the first cell and the second cell. Therefore, the X-ray photon amount that can be detected can be increased. That is, the information amount of the X-ray photons can be increased. As a result, the detection accuracy can be improved drastically.

In the case where the photon counting-type radiation detector has a three-layer structure, the X-rays that pass through the first cell and the second cell reach a third cell. In the case where the photon counting-type radiation detector has a structure of four or more layers, the X-rays that pass through the first, second, and third cells reach a fourth cell. The detection amount can be increased by increasing the cells transmitting the X-rays.

FIG. 3 is a schematic view showing another example of the photon counting-type radiation detector. In FIG. 3, 1 is the photon counting-type radiation detector. 1-1 is the first cell. 1-2 is the second cell. In FIG. 3, a space S is provided between the first cell 1-1 and the second cell 1-2. In the stacked structure of the photon counting-type radiation detector according to the embodiment, the cells above and below may be bonded; or the cells above and below may be separated. As long as the X-rays passing through the first cell can be detected by the second and subsequent cells, the specific structure of the photon counting-type radiation detector is modifiable as appropriate.

A two-layer type and a three-layer type are illustrated in FIG. 1 to FIG. 3. The upper limit of the number of stacks is not limited as long as the transmitted X-rays can be detected. Considering the ease of making the detector, it is favorable for the number of stacks to be 50 or less.

The thickness of the detector can be thin in the case of a single-body structure in which the cells are bonded to each other as in FIG. 1 and FIG. 2. Malfunctioning cells can be replaced easily in the case of a stacked structure in which the cells above and below are separated as in FIG. 3.

According to a stacked structure of cells such as that recited above, different X-ray photon information amounts can be acquired by the upper layer and the lower layer. Therefore, the time resolution can be increased. Also, X-rays are electromagnetic waves having wavelengths of 10 pm (picometers) to 10 nm (nanometers). X-rays of larger wavelengths easily pass through the cell. The wavelength of the X-rays to be detected can be adjusted by using a stacked structure. The resolution can be increased by this aspect as well.

Figure 4:
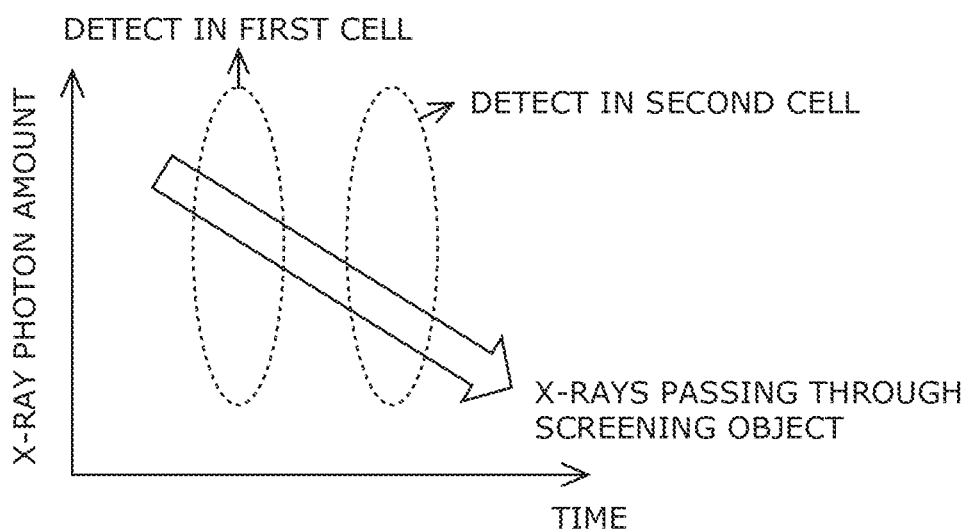
FIG. 4 is a conceptual view describing the time resolution of the photon counting-type radiation detector according to the embodiment.

FIG. 4 is a conceptual view describing the time resolution of the photon counting-type radiation detector according to the embodiment. The X-rays that pass through the screening object pass through the first cell and reach the second cell. The X-rays that pass through the screening object can be detected with a time difference between the first cell and the second cell. Therefore, the time resolution can be increased. Also, the time resolution can be increased further by increasing the number of stacks of the cells.

In an X-ray detector using a solid scintillator, the light emission of the solid scintillator where the X-rays are irradiated is changed into an electrical signal by a detection element. Therefore, a stacked structure of cells such as that of the embodiment cannot be used.

Figure 5:
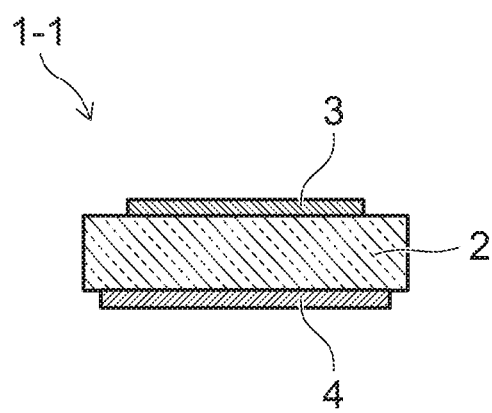
FIG. 5 is a schematic view showing an example of a cell according to the embodiment.
Figure 6:
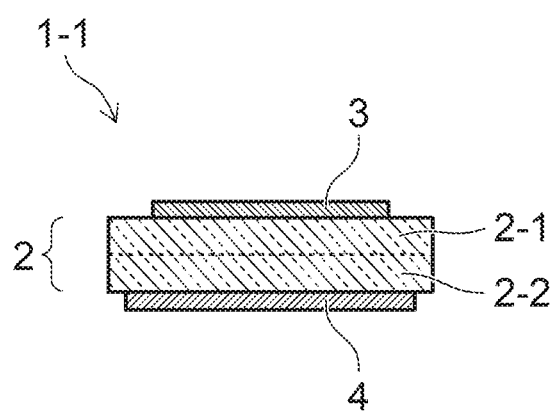
FIG. 6 is a schematic view showing another example of the cell according to the embodiment.

FIG. 5 and FIG. 6 are schematic views showing specific structures of cells. In FIG. 5 and FIG. 6, 1-1 is the first cell. 2 is an X-ray absorption layer. 2-1 is a first X-ray absorption layer. 2-2 is a second X-ray absorption layer. 3 is a front-side electrode. 4 is a backside electrode.

The cell includes the X-ray absorption layer, and electrode layers provided at the front and back surfaces of the X-ray absorption layer. The structure of the first cell is illustrated in FIG. 5 and FIG. 6. The structures of the second and subsequent cells also are similar.

The X-ray absorption layer 2 has the function of absorbing the X-rays and changing the X-rays into an electrical signal. It is favorable for the X-ray absorption layer 2 to include a SiC (silicon carbide) layer. The SiC layer functions as the X-ray absorption layer and has the ability to transmit X-rays. Therefore, a cell that includes a SiC layer in the X-ray absorption layer 2 is optimal as a cell that transmits the X-rays.

The bandgap of a SiC layer is larger than the bandgap of conventional CdTe. Although the bandgap of CdTe is 1.47 eV, the bandgap of SiC is 2 eV or more. Room-temperature operation is possible due to the large bandgap. Also, the leakage current can be small. When the leakage current is small, the applied voltage can be high. By setting the applied voltage to be high, the resolution can be increased because the tail toward the low-energy side disappears. Because the resolution can be increased, a detector that includes a SiC layer is favorable for direct photon counting. The direct photon counting directly detects the X-ray photons passing through the screening object. Conversely, a technique that uses a light-emitting substance emitting light due to the X-rays such as a solid scintillator and detects the light of the light-emitting substance is called indirect photon counting. The cell according to the embodiment may be used in an indirect photon counting-type radiation detector.

The specific resistance of SiC is larger than the specific resistance of CdTe. The specific resistance of SiC is, for example, not less than $1\times10^{11}$ Ωcm. By increasing the specific resistance, carrier recovery by a high electric field is possible. The dielectric constant of SiC is lower than the relative dielectric constant of CdTe. The dielectric constant of SiC is, for example, 12.0 or less. By reducing the dielectric constant, a high-speed operation by a small depletion capacity is possible. Furthermore, a detector that uses SiC can be used with both a Schottky type and a P-N junction-type.

2H, 3C, 4H, 6H, 8H, 10H, and 15R are examples of the crystal structure of SiC. It is favorable for the crystal structure to be one type selected from the group consisting of 3C, 4H, and 6H. Table 1 shows a comparison between the characteristics of SiC and the characteristics of CdTe.

TABLE 1

| | | | Material | | |
|---|---|---|---|---|---|
| | | | | SiC | |
| Item | Units | CdTe | 4H | 6H | 3C |
| Density | g/cm³ | 5.85 | | 3.21 | |
| Band gap | eV | 1.47 | 3.25 | 3.00 | 2.20 |
| Dielectric constant | | 14.1 | 10.0 | 9.7 | 9.6 |
| Mobility | cm²/Vs | n: 1000 p: 100 | n: 900$^a$, 650$^c$ p: 115 | n: 400$^a$, 50$^c$ p: 90 | n: 900 p: 300 |
| Minority carrier lifetime | s | n: 10⁻⁶ p: 10⁻⁷ | | n: 10⁻⁶ p: 10⁻⁶ | |
| Intrinsic carrier density | cm⁻³ | 7 × 10⁵ | 5 × 10⁻⁹ | 2 × 10⁻⁶ | 1.5 × 10⁻¹ |
| Specific resistance | Ωcm | 10⁹ | | 1 × 10¹¹ or more | |

As shown in Table 1, among 4H—SiC, 6H—SiC, and 3C—SiC, 4H or 6H is favorable. In particular, 4H is favorable. The bandgaps of 4H—SiC and 6H—SiC are respectively 3.25 eV and 3.00 eV. These bandgaps are larger than the bandgap of 3C—SiC.

The SiC layer may have a multilayer structure. FIG. 6 shows an example in which the X-ray absorption layer 2 has a two-layer structure of the first X-ray absorption layer 2-1 and the second X-ray absorption layer 2-2.

When a Schottky-type cell structure is used, it is favorable for the first X-ray absorption layer 2-1 to be the epitaxial SiC layer, and for the second X-ray absorption layer 2-2 to be a SiC layer. The SiC layer that is the second X-ray absorption layer is, for example, a SiC substrate. The epitaxial SiC layer is formed by epitaxially growing SiC on a SiC substrate. The depletion layer can be widened by forming the epitaxial layer. By widening the depletion layer, a higher-speed operation is possible. It is favorable for the thickness of the epitaxial layer (the first X-ray absorption layer 2-1) to be in the range not less than 5 and not more than 200 μm. If less than 5 μm, the effect of providing the epitaxial layer is insufficiently obtained. On the other hand, if 200 μm is exceeded, it is difficult to obtain a homogeneous epitaxial layer. The ability of the X-ray absorption layer degrades if the epitaxial layer is insufficiently homogeneous. Therefore, it is favorable for the thickness of the epitaxial SiC layer to be not less than 5 μm and not more than 200 μm. More favorably, the thickness is not less than 10 μm and not more than 100 μm. Also, it is favorable for the thickness of the SiC layer (the second X-ray absorption layer 2-2) to be 50 μm or more.

Also, the epitaxial SiC layer and the SiC layer are discriminable by observing the cross-sectional structures. The epitaxial SiC layer has a higher density. Therefore, the epitaxial SiC layer (the first X-ray absorption layer 2-1) functions mainly as the X-ray absorption layer. In the case where the epitaxial SiC layer (the first X-ray absorption layer 2-1) formed on the SiC layer (the second X-ray absorption layer 2-2) is sufficiently thick, the SiC layer (the second X-ray absorption layer 2-2) may be removed; and the epitaxial SiC layer single layer may be used as the X-ray absorption layer 2.

When a P-N junction-type cell structure is used, the first X-ray absorption layer 2-1 includes an n-type SiC layer; and the second X-ray absorption layer 2-2 includes a p-type SiC layer. Also, the first X-ray absorption layer 2-1 may include the p-type SiC layer; and the second X-ray absorption layer 2-2 may include the n-type SiC layer. It is favorable for the thickness of the p-type SiC layer to be not less than 5 μm and not more than 200 μm. Also, it is favorable for the thickness of the n-type SiC layer to be not less than 5 μm and not more than 200 μm.

An example in which the X-ray absorption layer 2 has a two-layer structure is described in FIG. 6. The X-ray absorption layer 2 may have a multilayer structure of three or more layers.

In the Schottky type, a high-speed operation is possible because the majority carriers have a rectifying action. In the P-N junction-type, the formation of the P layer and the N layer can be performed by ion implantation. Therefore, the suitability for mass production is excellent. Comparing the Schottky type and the P-N junction-type, the Schottky type is more favorable. In a cell used in an X-ray detector, it is necessary for the X-rays to strike the depletion layer. In the Schottky type, it is possible to widen the depletion layer by applying a voltage between the front-side electrode and the backside electrode. By using a Schottky-type cell including a SiC layer, the depletion layer can be widened sufficiently even for a low applied voltage of 300 V or less. For example, the depletion layer can be 3 μm or more by using a low voltage application of about 10 to 100 V. Also, in the Schottky type, the leakage current can be small.

A large voltage that exceeds 300 V may be applied to a cell including a SiC layer. For example, the cell that includes the SiC layer also can be used with an applied voltage of 1000 V or less.

Etching-patterning is possible for the SiC layer. The configuration of the SiC layer can be modified arbitrarily by etching-patterning. Therefore, the SiC layer can be used as a structure that suppresses the spreading of the carriers. Also, because etching-patterning is possible, the surface of the X-ray absorption layer 2 can be small.

It is also possible for a current amplifier to be built into the X-ray absorption layer 2. By the current amplifier being built-in, the generation of noise can be suppressed.

Figure 7:
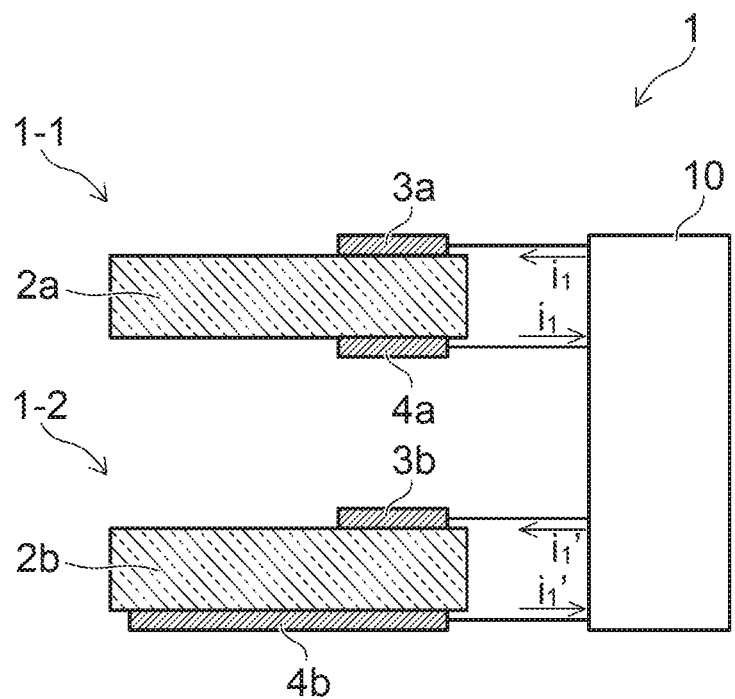
FIG. 7 is a schematic view showing an example of the overall configuration of the photon counting-type radiation detector according to the embodiment.

FIG. 7 is a schematic view showing an example of the overall configuration of the photon counting-type radiation detector according to the embodiment. In FIG. 7, 1 is the photon counting-type radiation detector. 1-1 is the first cell. 1-2 is the second cell. FIG. 7 shows the structure in the case where the first cell and the second cell are viewed from the side which is a direction different from that of FIG. 1 to FIG. 3, FIG. 5, and FIGS. 6. 2a, 3a, and 4a are respectively the X-ray absorption layer, the front-side electrode, and the backside electrode of the first cell. 2b, 3b, and 4b are respectively the X-ray absorption layer, the front-side electrode, and the backside electrode of the second cell. 10 is the controller. The front-side electrode and the backside electrode of each cell are connected to the controller 10. The voltage between the front-side electrode and the backside electrode of each cell is applied by the controller 10.

As shown in FIG. 7, the X-rays that pass through the screening object are incident on the first cell. A portion of the incident X-rays is absorbed by the X-ray absorption layer of the first cell. The remaining X-rays are incident on the second cell. At least a portion of the X-rays incident on the second cell are absorbed by the X-ray absorption layer of the second cell.

In the first cell, carriers (electrons and holes) are generated in the X-ray absorption layer when the X-rays are absorbed by the X-ray absorption layer. The electrons and the holes flow respectively in the front-side electrode and the backside electrode. Thereby, as shown in FIG. 7, a current $i_1$ flows between the controller, the front-side electrode, and the backside electrode. In other words, the X-rays are converted into an electrical signal in the X-ray absorption layer. The controller detects the magnitude of the current $i_1$.

Similarly, a current $i_1'$ flows between the controller, the front-side electrode, and the backside electrode when the X-rays are absorbed by the X-ray absorption layer in the second cell. The controller detects the magnitude of the current $i_1'$. The magnitude of the current $i_1$ and the magnitude of the current $i_1'$ are proportional to the amount of the X-rays passing through the screening object.

The directions of the currents $i_1$ and $i_1'$ and the voltage applied between the front-side electrode and the backside electrode are modifiable as appropriate.

One type selected from the group consisting of a metal, a metal carbide, and a metal silicide is favorable as the electrode material. Among these, a metal carbide or a metal silicide is favorable. That is, it is favorable for the front-side electrode 3 and the backside electrode 4 to include carbon or silicon as elemental components. By including carbon or silicon as an elemental component of the electrode, reactions between the SiC layer and the electrode can be suppressed.

One type selected from the group consisting of Ti (titanium), W (tungsten), Mo (molybdenum), Ta (tantalum), and Nb (niobium) is favorable as the metal electrode material. One type selected from the group consisting of TiC (titanium carbide), WC (tungsten carbide), $Mo_2C$ (molybdenum carbide), TaC (tantalum carbide), and NbC (niobium carbide) is favorable as the metal carbide electrode material. Also, one type selected from the group consisting of $TiSi_2$ (titanium silicide), $WSi_2$ (tungsten silicide), $MoSi_2$ (molybdenum silicide), $TaSi_2$ (tantalum silicide), and $NbSi_2$ (niobium silicide) is favorable as the metal silicide electrode material. Among these, titanium carbide, tungsten carbide, titanium silicide, or tungsten silicide is particularly favorable.

The electrode layer can be formed by sputtering the metal, the metal carbide, and the metal silicide recited above. Other than sputtering, CVD, ion plating, vapor deposition, thermal spraying, plating, etc., also are applicable to form the electrode layer.

The melting point is high for the metal, the metal carbide, and the metal silicide recited above. By using a material having a high melting point as the electrode material, alteration of the electrode does not occur easily even when heat treatment is performed in the manufacturing processes of the cell including the SiC layer. The electrode that is made of the metal carbide or the metal silicide can suppress reactions with the SiC layer in the manufacturing processes of the cell and/or when using (when energizing) the X-ray detector. Therefore, stable electrical characteristics are obtained. Furthermore, the life of the cell can be longer.

In the case where the front-side electrode and the backside electrode of the cell include the metal, the metal carbide, or the metal silicide recited above, the transmissivity to X-rays is not high. Therefore, in the cell transmitting the X-rays, the front-side electrode and the backside electrode are provided only in a portion of the X-ray absorption layer as shown in FIG. 7.

In the first cell, it is favorable for at least a portion of the front-side electrode and at least a portion of the backside electrode to oppose each other in the travel direction of the X-rays. According to this configuration, the X-rays that pass through the X-ray absorption layer and travel toward the second cell are not reflected easily by the backside electrode. The detection efficiency of the X-rays can be increased thereby.

It is favorable for at least a portion of the front-side electrode of the second cell and at least a portion of the backside electrode of the first cell to oppose each other in the travel direction of the X-rays. According to this configuration, the X-rays that pass through the first cell are not reflected easily by the backside electrode of the second cell. The detection efficiency of the X-rays can be increased further thereby.

It is favorable for the surface area of the backside electrode to be greater than the surface area of the front-side electrode for a cell (the lowermost cell of the stacked structure) in which it is unnecessary to transmit the X-rays. In the example shown in FIG. 7, the second cell is a cell in which it is unnecessary to transmit the X-rays. By setting the surface area of the backside electrode of the second cell to be greater than the surface area of the front-side electrode, the X-rays can be suppressed from passing further. The unfavorable effects on the other members which are on the backside of the second cell can be prevented thereby. For example, by setting the thickness of the backside electrode to be greater than the thickness of the front-side electrode, it is more difficult for the X-rays to pass through the backside electrode. It is desirable for the backside electrode to include a material that does not transmit the X-rays easily. Tungsten, molybdenum, lead, a tungsten compound (WC, $WSi_2$, etc.), and a molybdenum compound ($Mo_2C$, $MoSi_2$, etc.) are examples of such a material. A layer that does not transmit the X-rays and includes these materials may be provided in the backside electrode as well.

Also, in the case where the X-rays pass through the second cell, it is favorable for at least a portion of the front-side electrode and at least a portion of the backside electrode to oppose each other in the travel direction of the X-rays in the second cell as well.

An insulating film may be provided at a portion of the bonding interface between the front-side electrode 3 and the X-ray absorption layer 2. Similarly, an insulating film may be provided at a portion of the bonding interface between the backside electrode 4 and the X-ray absorption layer 2. By providing the insulating film, the Schottky-type structure is formed easily. Silicon oxide ($SiO_2$) is an example of the insulating film.

For the Schottky type, the width of the front-side electrode 3 can be narrow. By setting the width of the front-side electrode 3 to be narrow, the X-ray detection surface of the cell can be downsized. For example, the width of the front-side electrode 3 can be 250 μm or less. It is also possible to set the width to be 100 μm or less. Furthermore, by using etching-patterning technology, the width of the front-side electrode 3 can be 10 μm or less. It is also possible to set the width to be less than 1 μm (sub-micron). By reducing the front-side electrode, the X-ray detection surface can be small. By downsizing the X-ray detection surface, a high-resolution image can be obtained. That is, a sub-micron spatial resolution can be obtained. The width of the front-side electrode 3 corresponds to a width L of the front-side electrode 3 provided between the insulating layer 6 shown in FIG. 10.

It is favorable for the thicknesses of the front-side electrode 3 and the backside electrode 4 each to be 50 nm or less. By presetting these electrode layers to be thin, the proportion of the shielded X-rays can be suppressed.

Oxidation prevention films may be provided at the surfaces of these electrodes as necessary. A metal nitride film, a resin film, etc., are examples of the oxidation prevention film.

A cell that includes a SiC layer such as that described above can detect X-ray photons and can transmit X-rays. Therefore, this is favorable for a cell transmitting X-rays. In the case where multiple cells are stacked, a SiC layer is provided in the cell(s) transmitting the X-rays. Other than SiC, examples of the X-ray absorption layer used in the cell transmitting the X-rays include diamond, GaAs (gallium arsenide), GaN (gallium nitride), and $Ga_2O_3$ (gallium oxide). In the case where a stacked structure of multiple cells is formed, a cell that includes a diamond layer or a GaAs layer may be included in a portion of the multiple cells. Diamond is expensive; and GaAs is unfavorable environmentally because arsenic is used. Considering the price and the environment, it is favorable to use a cell including a SiC layer.

A SiC layer may or may not be included in a cell (the lowermost cell of the stacked structure) in which it is unnecessary to transmit X-rays. A cell that includes one selected from the group consisting of a CdTe layer, a diamond layer, a GaAs layer, a GaN layer, and a $Ga_2O_3$ layer is an example of a cell not using a SiC layer.

In the case where the cells above and below are bonded as in FIG. 1 (or FIG. 2), an insulating member is provided so that the backside electrode of the first cell and the front-side electrode of the second cell do not conduct. An epoxy resin is an example of the insulating member.

Figure 8:
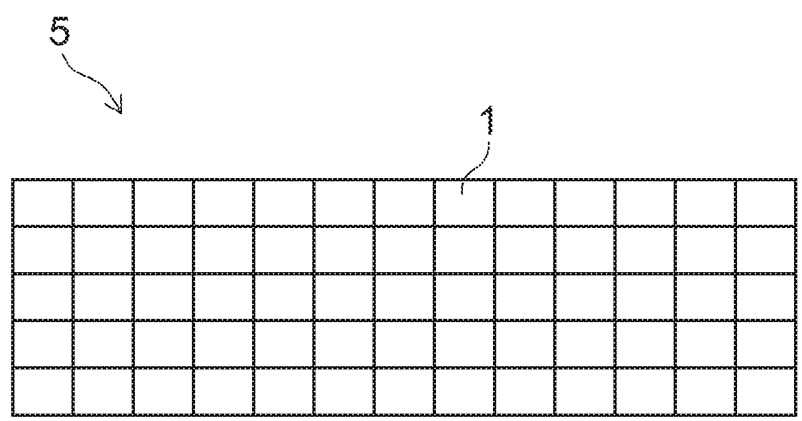
FIG. 8 is a schematic view showing an example of a detector array according to the embodiment.
Figure 9:
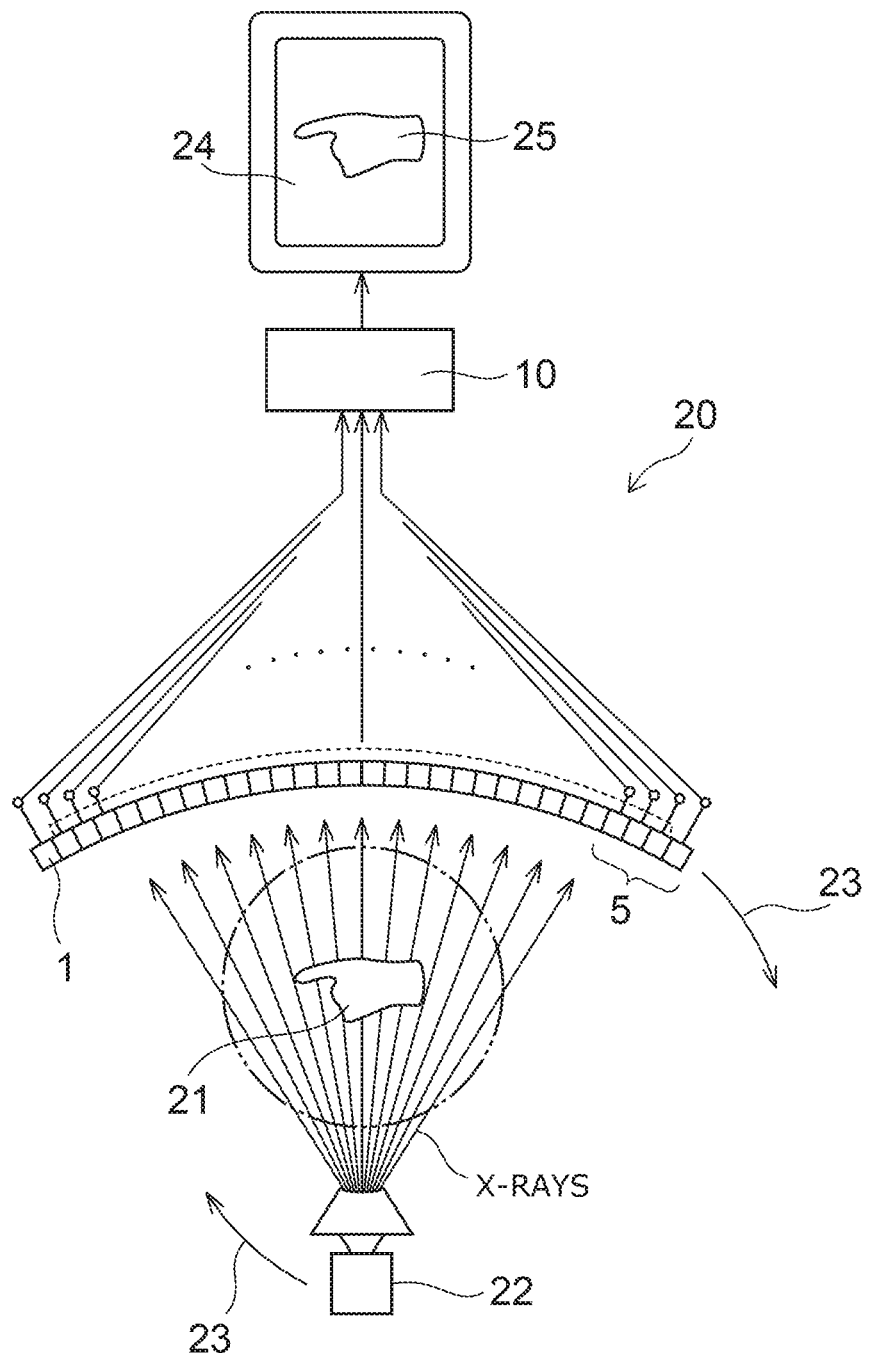
FIG. 9 is a schematic view showing an example of a radiation detection device according to the embodiment.

A detector array is configured by arranging, in the in-plane direction, multiple radiation detectors having stacked structures such as that described above. FIG. 8 is a schematic view showing an example of a detector array. In FIG. 8, 1 is the photon counting-type radiation detector. 5 is the detector array. In the detector array 5, the detectors 1 in which cells are stacked are arranged two-dimensionally longitudinally and laterally. A radiological inspection device has a structure in which multiple detector arrays 5 are arranged. For example, medical devices and industrial non-destructive inspection devices are examples of X-ray inspection devices. FIG. 9 is a schematic view showing an example of a radiological inspection device. In FIG. 9, 20 is a radiological inspection device (a CT device). 1 is the photon counting-type radiation detector. 5 is the detector array. 10 is the controller. 21 is a screening object. 22 is a radiation tube. 24 is a display. 25 is an image. The screening object is fixed between the radiation tube and multiple radiation detectors. The radiation tube emits X-rays. The emitted X-rays are irradiated on the screening object. The X-rays that pass through the screening object are incident on the radiation detector. Each radiation detector is connected to the controller. The current that flows in each cell of each radiation detector is detected by the controller. The controller generates an image of the screening object based on the detected currents. The controller displays the generated image on the display. For a fixed screening object, the radiation tube and the radiation detector may be rotatable. 23 shows the rotation direction of the radiation tube and the radiation detector. By rotating the radiation tube and the radiation detector with respect to the screening object, the screening object can be inspected from different angles.

Because the photon counting-type radiation detector 1 has a stacked structure of cells, more information of the X-rays passing through the screening object can be detected. Because the information amount of the X-ray photons of each photon counting-type radiation detector can be increased, the detection accuracy of the detector array and the radiological inspection device can be improved drastically. Additionally, much detection current can be obtained at one time in each detector. As a result, the time resolution increases. Furthermore, the measurement time can be short because the information amount of the X-ray photons obtained at one time is increased. Therefore, the exposure amount of the screening object can be low.

It is also possible to form the structure arranged two-dimensionally longitudinally and laterally by etching-patterning the SiC layer.

Also, as described above, the detection area can be small by setting the width L of the front-side electrode 3 to be small. For example, the width L is set to be 250 μm or less, 100 μm or less, 10 μm or less, or less than 1 μm. By setting the detection area to be small, high-resolution detecting is possible. By setting the width L of the front-side electrode 3 to be less than 1 μm, the image that can be detected can have a high definition that is less than 1 μm. Because the front-side electrode is small, the X-ray detection surface can be small. Because higher definition that is less than 1 μm is possible, the detection of micro cancer cells also is possible. For example, the detection of micro cancer cells is difficult in conventional mammography. Therefore, palpation has been the main form of breast cancer screening. Higher definition is possible in the X-ray inspection device according to the embodiment. Therefore, this is favorable also in an inspection device detecting micro cancer cells such as mammography, etc.

The X-ray detection capability of a cell using a SiC layer will now be described. For example, in the case where the energy of the X-rays is about 40 keV, the thickness of SiC necessary to absorb all of the X-rays is about 8 cm. In the case where the energy of the X-rays is about 60 keV, the thickness of SiC necessary to absorb all of the X-rays is about 29 cm. In other words, the X-rays can be caused to pass through the X-ray absorption layer by setting the thickness of the X-ray absorption layer to be a thickness that does not absorb all of the X-rays.

$I_1(z)=I_1\exp(-t/\lambda)$, where the intensity of the incident X-rays is $I_1$, the film thickness of the cell is t, and the attenuation coefficient of the X-rays is $\lambda$. That is, the intensity of the incident X-rays is reduced by passing through the cell.

For example, the attenuation coefficient $\lambda$ of the X-rays is 27 mm when the thickness t of the SiC layer is set to 1 mm and the intensity $I_1$ of the incident X-rays is set to 38 keV. $I_1'=0.96I_1$, where the intensity of the X-rays passing through the SiC layer of the first layer is $I_1'$. $I_1''=0.93I_1$, where the intensity of the X-rays passing through the SiC layer of the second layer is $I_1''$. Attenuated X-rays can be measured by increasing the number of stacks. Also, the detection current in the SiC layer of the first layer is taken as $i_1$; and the detection current of the SiC layer of the second layer is taken as $i_1'$. The detection current in the SiC layer of the second layer is $i_1'=1.96i_1$. As theoretical values, the detection current values can be changed by using such a stacked structure.

It is also possible to detect X-rays of two wavelengths. There is a technique of increasing the detection current by using two types of X-ray energy. A CT device that uses such a technique is called a dual energy (Dual Energy) CT. In the dual technique CT, X-rays of two types of energy are emitted simultaneously or alternately from a radiation tube.

For example, the thickness t of the SiC layer is set to 1 mm; the intensity $I_1$ of the incident X-rays is set to 38 keV; and the intensity $I_2$ is set to 59 keV. For the X-ray intensity of 38 keV, the intensity of the X-rays passing through the first layer is $0.96I_1$; and the intensity $I_1''$ of the X-rays passing through the second layer is $0.93I_1$. Also, for the X-ray intensity of 59 keV, the intensity $I_2'$ of the X-rays passing through the first layer is $0.99I_2$; and the intensity $I_2''$ of the X-rays passing through the second layer is $0.98I_2$. The detection current of the first layer due to the X-rays having the intensity of 38 keV is taken as $i_1$. The detection current of the first layer due to the X-rays having the intensity of 59 keV is taken as $i_2$. The detection current i of the first layer is represented by $i=i_1+i_2$. $i \propto 2.33I_1+I_2$. The detection current of the second layer due to the X-rays having the intensity of 38 keV is taken as $i_1'$. The detection current of the second layer due to the X-rays having the intensity of 59 keV is taken as $i_2'$. The detection current of the second layer is represented by $i'=i_1'+i_2'$. $i' \propto 2.26I_1+I_2$. $\propto$ is a symbol indicating proportionality. The information of the two wavelengths can be obtained by comparing the detection current i and the detection current i'. Even in the dual technique, the detection current can be increased by using the transmissive structure.

Here, although the X-ray intensity is illustrated as 38 and 59 keV, the detection current can be increased similarly even when changing the X-ray intensity.

The structure in FIG. 1 to FIG. 3 is a structure in which the X-rays are irradiated from the front-side electrode 3 side. The detector according to the embodiment is not limited to such a structure; and the X-rays may be irradiated from the side-surface direction of the X-ray absorption layer 2. In such a case, the multiple cells are stacked in the side-surface direction. In other words, the side-surface direction is a direction perpendicular to the direction connecting the front-side electrode and the backside electrode. The photon counting-type radiation detector may include both a stacked structure for detecting the X-rays irradiated from the front-side electrode 3 side and a stacked structure for detecting the X-rays irradiated from the side-surface direction of the X-ray absorption layer 2.

Also, although a detector using X-rays is described above, similar effects are obtained for a detector using gamma rays as well. Also, this is not limited to a CT device; and similar effects are obtained for a PET device as well.

EXAMPLES

Examples 1 to 8

Figure 10:
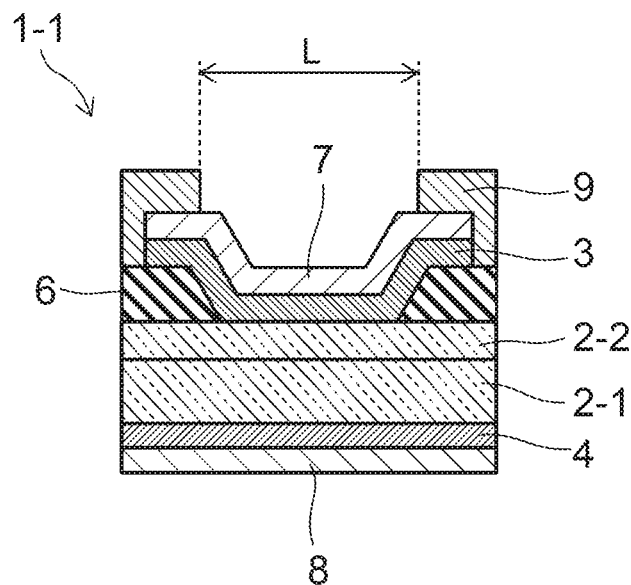
FIG. 10 is a schematic view showing an example of a Schottky-type cell according to the embodiment.

The Schottky-type cell shown in FIG. 10 was made as an example. In FIG. 10, 1-1 is the first cell. The 2-1 is the first X-ray absorption layer. 2-2 is the second X-ray absorption layer. 3 is the front-side electrode. 4 is the backside electrode. 6 is the insulating layer. 7 is a front-side oxidation prevention film. 8 is a backside oxidation prevention film. 9 is a front-side interconnect.

A 4H—SiC substrate (having a thickness of 300 μm and a specific resistance of $1.0 \times 10^{16}$ cm$^{-3}$) was used as the first X-ray absorption layer 2-1. An epitaxial SiC layer (having a thickness of 30 μm) was formed as the second X-ray absorption layer 2-2. The stacked body of the stacked body of the epitaxial SiC layer/4H—SiC substrate was etched into an array in which one cell unit is 250 μm long×250 μm wide.

Then, silicon oxide ($SiO_2$ having a thickness of 40 nm) was formed as the insulating layer 6.

Then, the front-side electrode 3 and the backside electrode 4 shown in Table 2 were formed by sputtering. The front-side electrode 3 size was set to 100 μm×100 μm. The width L is 100 μm. The size of the backside electrode 4 was set to 206 μm×206 μm. Titanium nitride (TiN having a thickness of 50 nm) was formed by sputtering as the front-side oxidation prevention film 7 and the backside oxidation prevention film 8 at the electrode surfaces. Also, the front-side interconnect 9 was formed as an extraction interconnect of the front-side electrode 3. The front-side interconnect 9 is an Al interconnect. The Al interconnect is formed by vacuum vapor deposition.

The cell for the examples was made by the processes recited above.

TABLE 2

|  | Front-side electrode (thickness) | Backside electrode (thickness) |
| --- | --- | --- |
| Example 1 | Ti (20 nm) | Ti (20 nm) |
| Example 2 | TiC (20 nm) | TiC (20 nm) |
| Example 3 | $TiSi_2$ (20 nm) | $TiSi_2$ (20 nm) |
| Example 4 | Mo (20 nm) | Mo (20 nm) |
| Example 5 | $Mo_2C$ (20 nm) | $Mo_2C$ (20 nm) |
| Example 6 | W (20 nm) | W (20 nm) |
| Example 7 | WC (20 nm) | WC (20 nm) |
| Example 8 | $W_2C$ (20 nm) | $W_2C$ (20 nm) |

The electrode of the cell of the example 1 is made of Ti (titanium). The electrode of the cell of the example 2 is made of TiC (titanium carbide). The electrode of the cell of the example 3 is made of $TiSi_2$ (titanium silicide). The electrode of the cell of the example 4 is made of Mo (molybdenum). The electrode of the cell of the example 5 is made of $Mo_2C$ (molybdenum (II) carbide). The electrode of the cell of the example 6 is made of W (tungsten). The electrode of the cell of the example 7 is made of WC (tungsten carbide). The electrode of the cell of the example 8 is made of $W_2C$ (tungsten (II) carbide).

Figure 11:
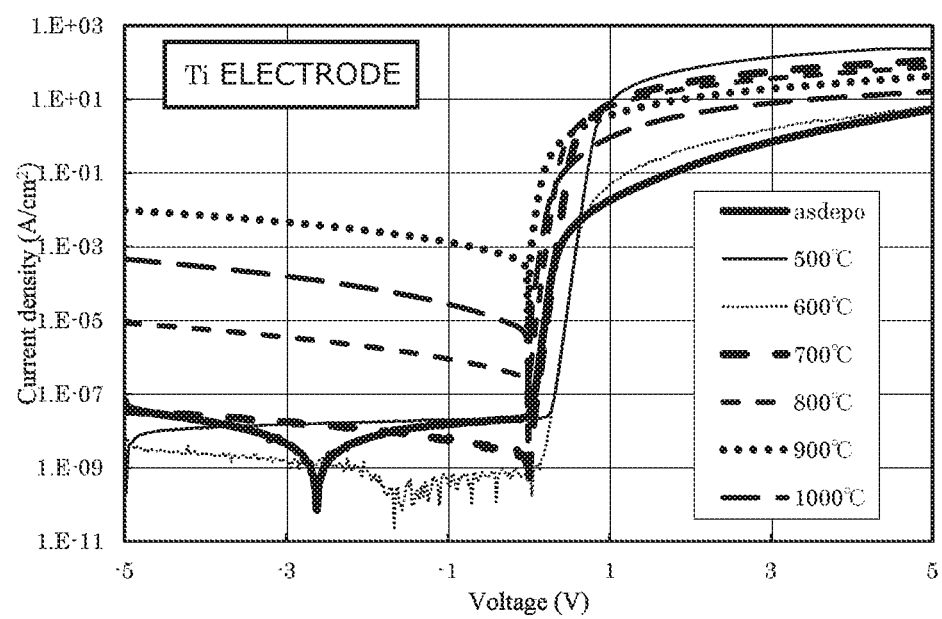
FIG. 11 is a figure showing the I-V characteristic for each heat treatment temperature of the Schottky-type cell according to an example 1 (a Ti electrode)
Figure 12:
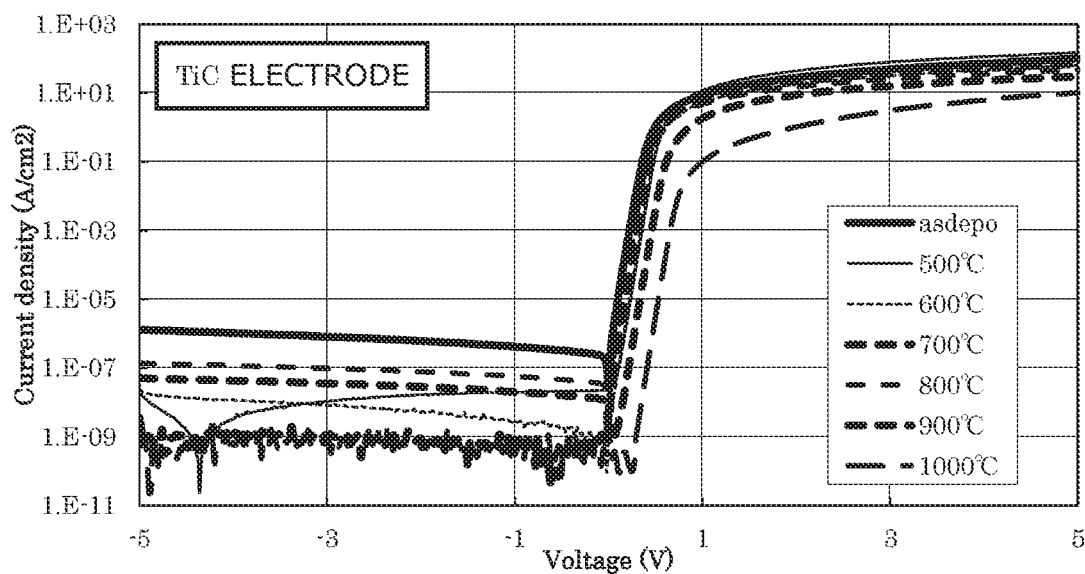
FIG. 12 is a figure showing the I-V characteristic for each heat treatment temperature of the Schottky-type cell according to an example 2 (a TiC electrode)
Figure 13:
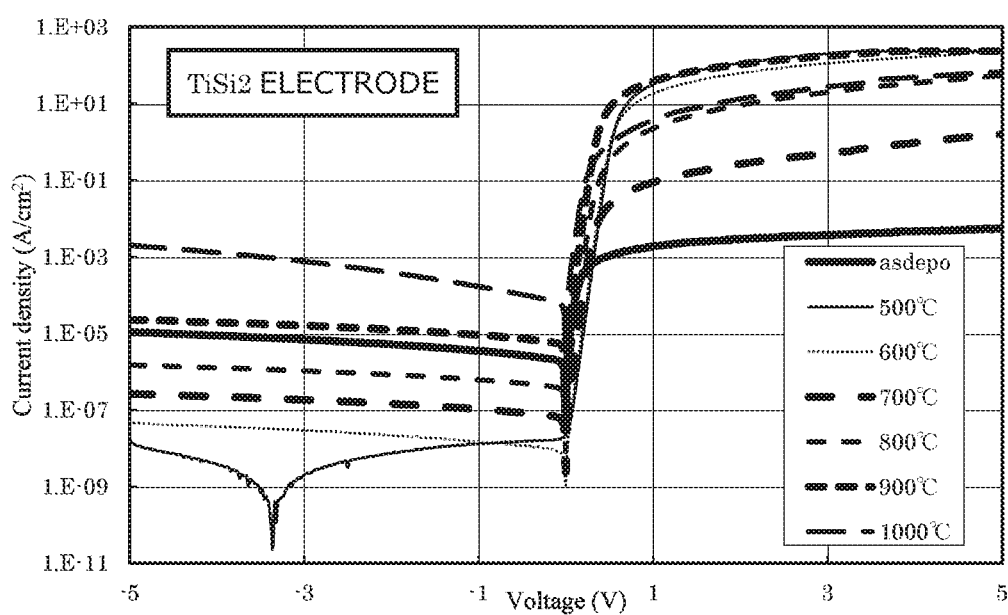
FIG. 13 is a figure showing the I-V characteristic for each heat treatment temperature of the Schottky-type cell according to an example 3 (a $TiSi_2$ electrode)
Figure 14:
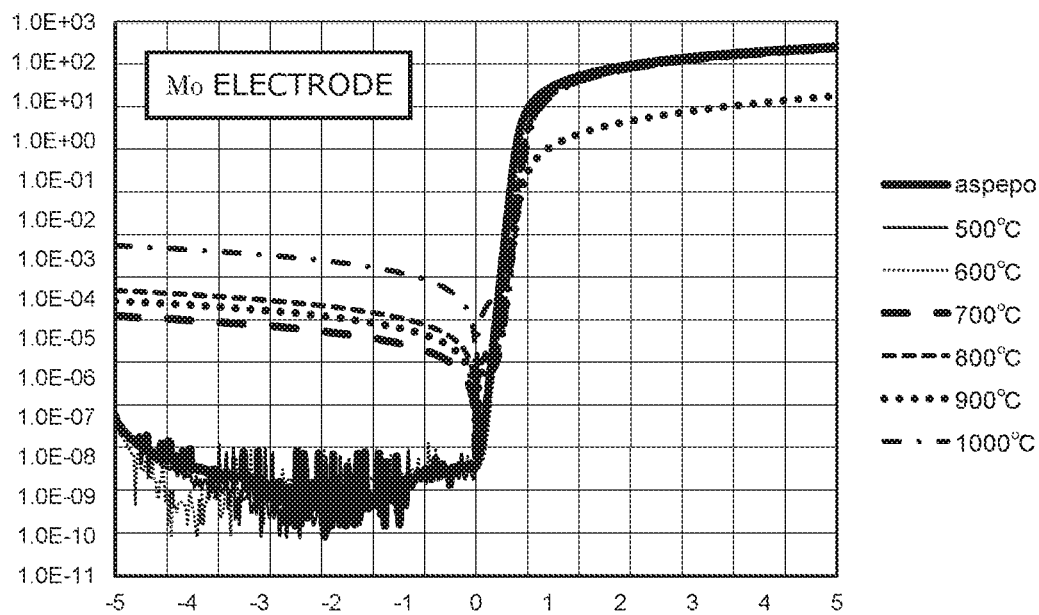
FIG. 14 is a figure showing the I-V characteristic for each heat treatment temperature of the Schottky-type cell according to an example 4 (a Mo electrode)
Figure 15:
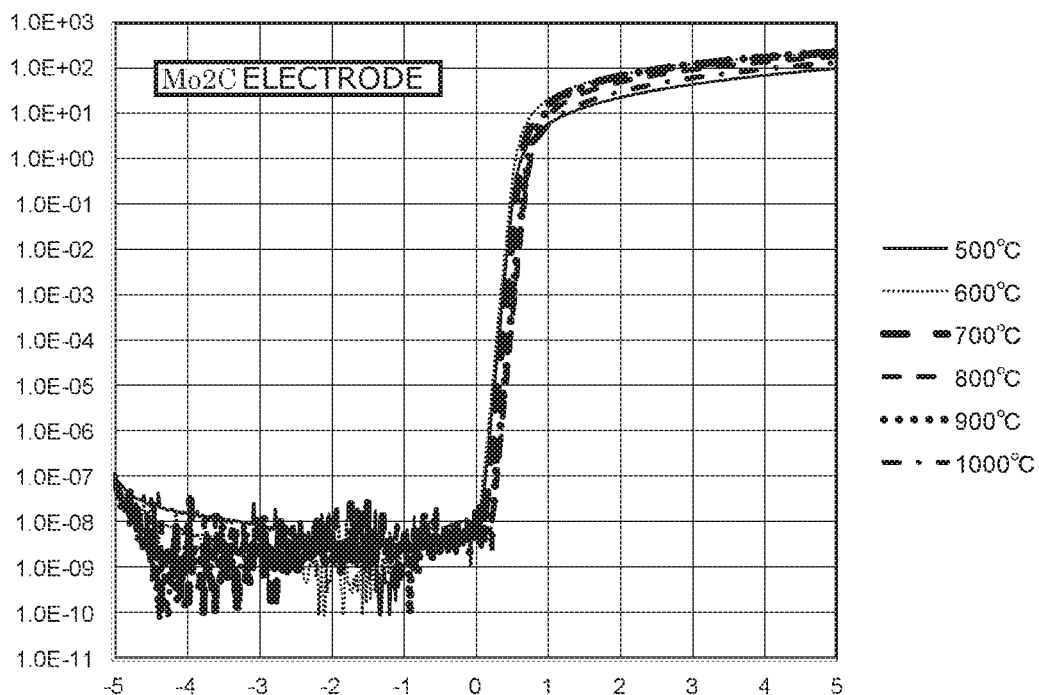
FIG. 15 is a figure showing the I-V characteristic for each heat treatment temperature of the Schottky-type cell according to an example 5 (a $Mo_2C$ electrode)
Figure 16:
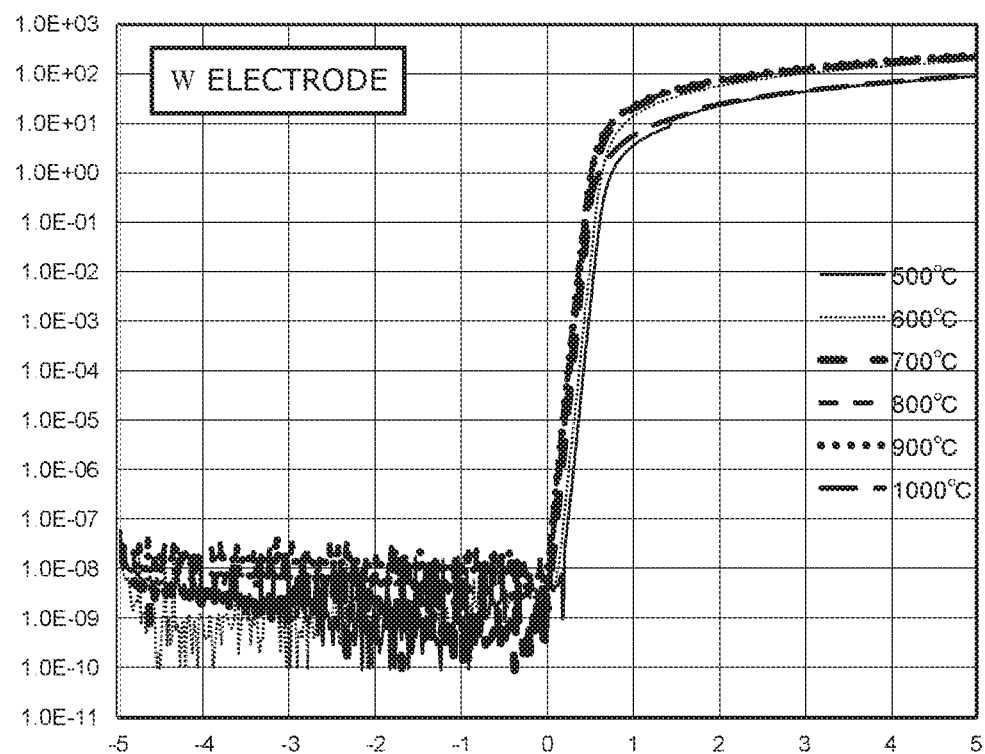
FIG. 16 is a figure showing the I-V characteristic for each heat treatment temperature of the Schottky-type cell according to an example 6 (a W electrode)
Figure 17:
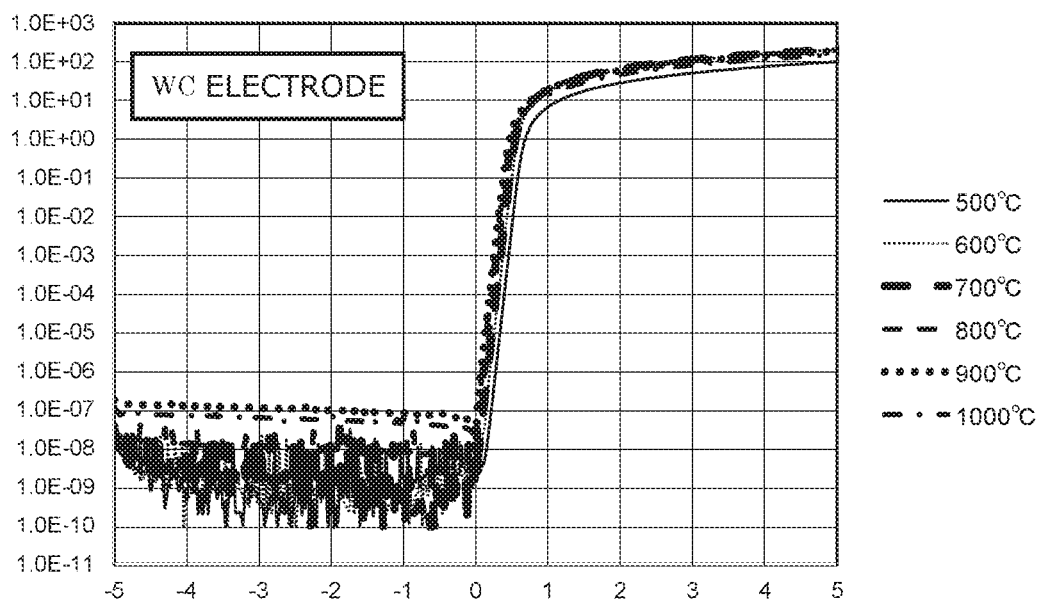
FIG. 17 is a figure showing the I-V characteristic for each heat treatment temperature of the Schottky-type cell according to an example 7 (a WC electrode)
Figure 18:
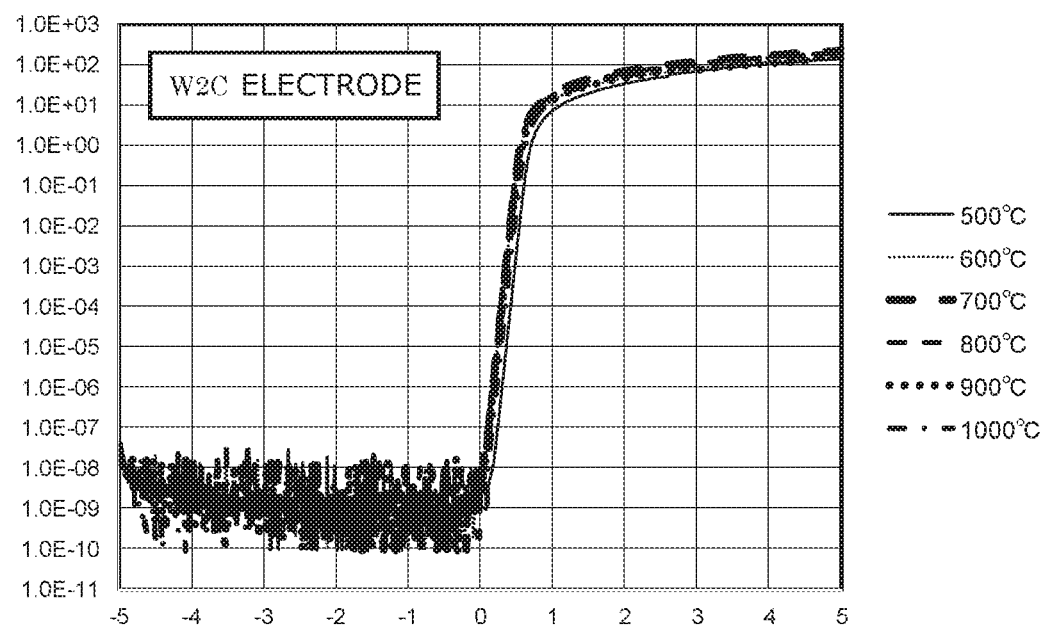
FIG. 18 is a figure showing the I-V characteristic for each heat treatment temperature of the Schottky-type cell according to an example 8 (a $W_2C$ electrode)

The I-V characteristic of the cell was verified for the examples 1 to 8. The I-V characteristic of the cell was verified after heat treatment for 1 minute in a nitrogen atmosphere at the temperatures of 500° C., 700° C., 800° C., 900° C., and 1000° C. The I-V characteristic of a cell for which heat treatment was not performed also was verified. The results are shown in FIG. 11 to FIG. 18. FIG. 11 shows the characteristics of the cell of the example 1. FIG. 12 shows the characteristics of the cell of the example 2. FIG. 13 shows the characteristics of the cell of the example 3. FIG. 14 shows the characteristics of the cell of the example 4. FIG. 15 shows the characteristics of the cell of the example 5. FIG. 16 shows the characteristics of the cell of the example 6. FIG. 17 shows the characteristics of the cell of the example 7. FIG. 18 shows the characteristics of the cell of the example 8. In FIG. 11 to FIG. 18, the horizontal axis is the voltage (voltage (V)); and the vertical axis is the current density (Current density (A/cm 2)). In FIG. 11 to FIG. 14, as depo shows the characteristic of the cell for which heat treatment is not performed.

It can be seen from the figures that the increasing trend of the reverse leakage current is small for the TiC electrode and the $TiSi_2$ electrode compared to the Ti electrode. In particular, the trend is pronounced in the high-temperature environment of 800° C. or more. On the other hand, a large difference is not seen at 500° C.

As a result, any of the Ti electrode, the TiC electrode, or the $TiSi_2$ electrode is usable as the electrode. The increasing trend of the reverse leakage current is small for the TiC electrode and the $TiSi_2$ electrode. This is because the reactions between the electrode material and the SiC layer are suppressed when using the cell. Comparing the TiC electrode and the $TiSi_2$ electrode, the increasing trend of the reverse leakage current is smaller for the TiC electrode. Therefore, it can be seen that the metal carbide electrode is most favorable.

For the Mo electrode, the increasing trend of the reverse leakage current was small at 600° C. or less. In the $Mo_2C$ electrode, the increasing trend of the reverse leakage current was small for all temperatures. This is because the $Mo_2C$ electrode suppresses reactions with the SiC layer. On the other hand, the experiment results show that the Mo electrode reacts easily with SiC as the temperature increases. Although either the Mo electrode or the $Mo_2C$ electrode is usable as the electrode, it is desirable for the heat treatment temperature to be 600° C. or less in the case where the Mo electrode is used.

Also, any of the W electrode, the WC electrode, or the $W_2C$ electrode is usable. It can be seen that tungsten or tungsten carbide suppresses reactions with the SiC layer. Comparing the W electrode, the WC electrode, and the $W_2C$ electrode, the increasing trend of the reverse leakage current was smallest for the $W_2C$ electrode. This is because the $W_2C$ electrode does not react easily with the SiC layer.

From the results recited above, it can be seen that the metal carbide is the most favorable electrode material. In other words, also, particularly the increasing trend of the reverse leakage current is suppressed for the $W_2C$ electrode and the $Mo_2C$ electrode. These two do not react easily with the SiC layer at a high temperature; therefore, the manufacturing conditions can be designed more freely.

Figure 19:
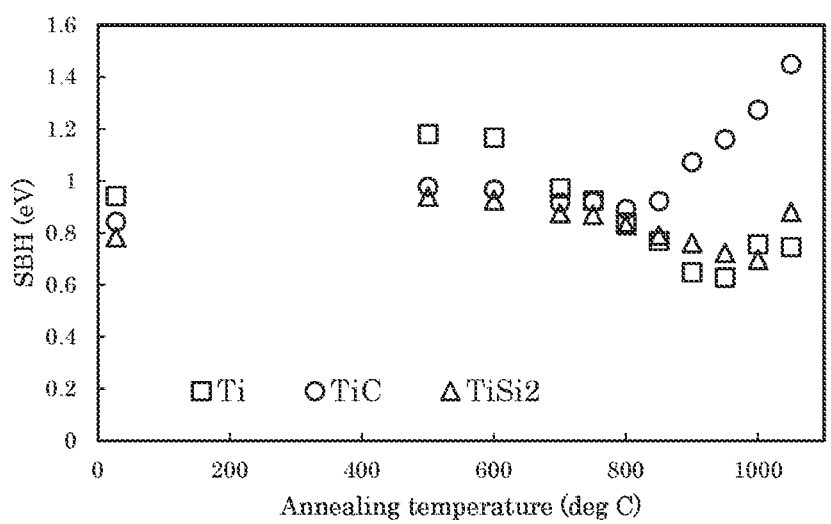
FIG. 19 is a figure showing an example of the relationship between the heat treatment temperature and the Schottky barrier value of the Schottky-type cell according to the examples 1 to 3.
Figure 20:
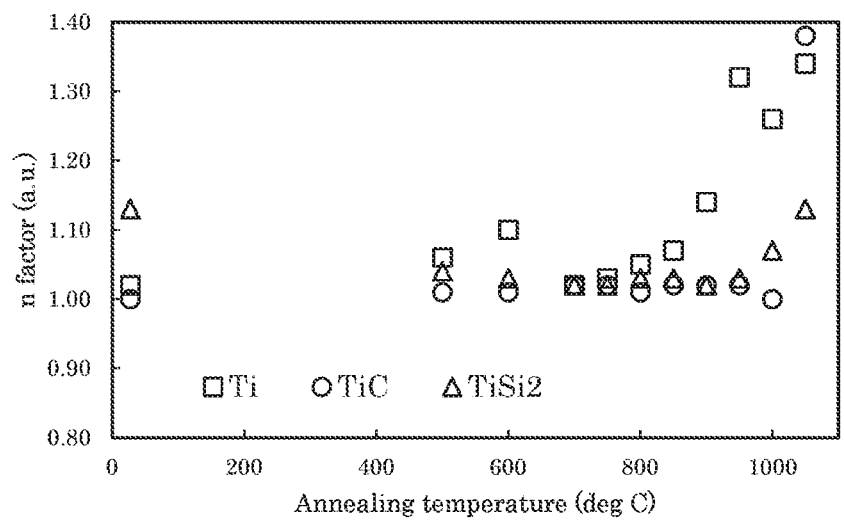
FIG. 20 is a figure showing an example of the relationship between the heat treatment temperature and the n-factor of the Schottky-type cell according to the examples 1 to 3.
Figure 21:
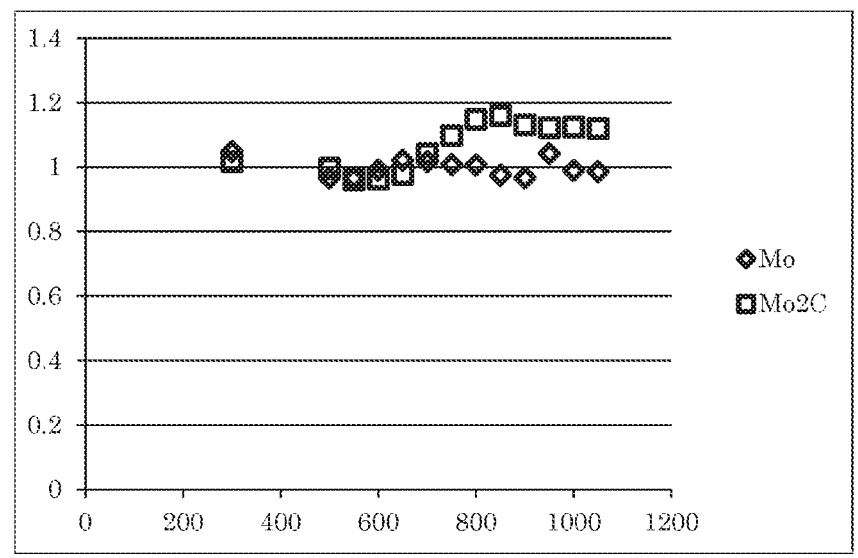
FIG. 21 is a figure showing an example of the relationship between the heat treatment temperature and the Schottky barrier value of the Schottky-type cell according to the examples 4 to 5.
Figure 22:
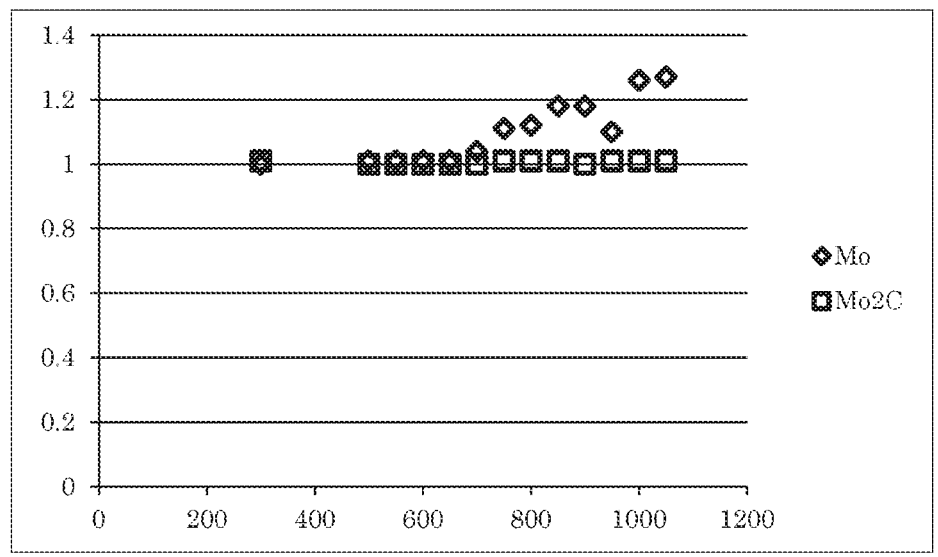
FIG. 22 is a figure showing an example of the relationship between the heat treatment temperature and the n-factor of the Schottky-type cell according to the examples 4 to 5.
Figure 23:
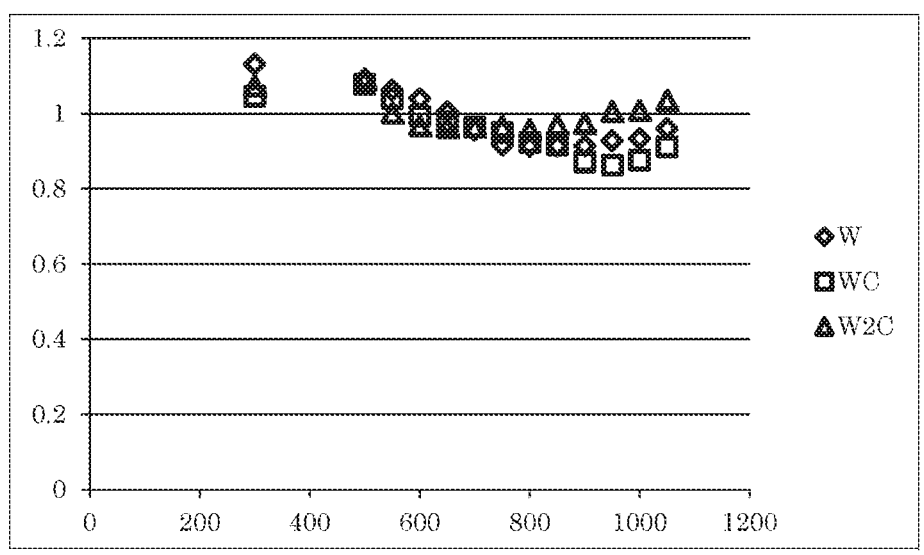
FIG. 23 is a figure showing an example of the relationship between the heat treatment temperature and the Schottky barrier value of the Schottky-type cell according to the examples 6 to 8.
Figure 24:
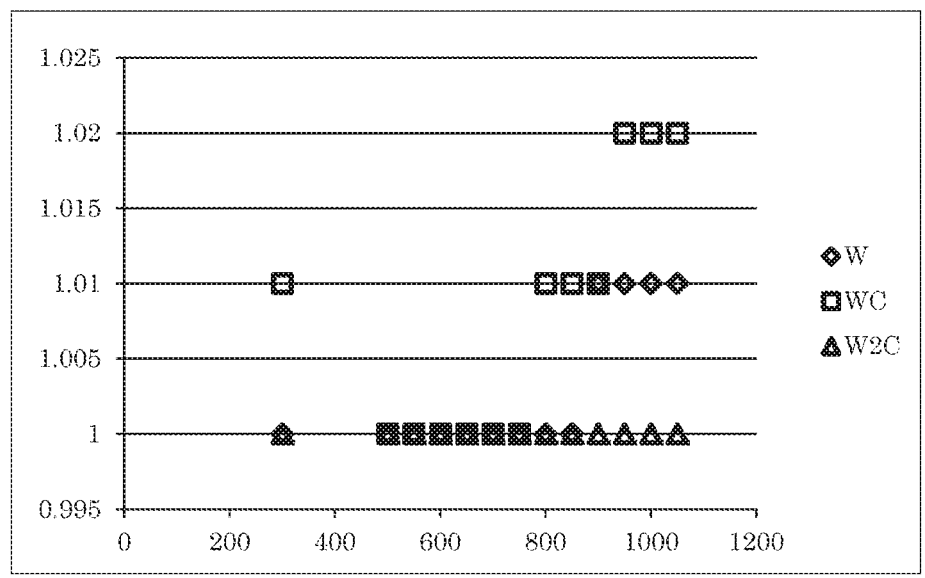
FIG. 24 is a figure showing an example of the relationship between the heat treatment temperature and the n-factor of the Schottky-type cell according to the examples 6 to 8.

Also, the relationship between the heat treatment temperature (° C.), a Schottky barrier value ϕB (eV), and the n-factor (a.u) is shown in FIG. 19 to FIG. 24. In the experiment, a cell for which heat treatment was performed for 1 minute in a nitrogen atmosphere at 500 to 1050° C. was used. In the experiment, the Schottky barrier value ϕB (eV) was measured when −1.0 V was applied to the cell at room temperature. The Schottky diode equation and the reverse saturation current (TED model) equation were used to calculate the Schottky barrier value. The n-factor was determined using a theoretical value of 1. FIG. 19 and FIG. 20 are graphs relating to the examples 1 to 3. FIG. 21 and FIG. 22 are graphs relating to the examples 4 to 5. FIG. 23 and FIG. 24 are graphs relating to the examples 6 to 8.

Also, FIG. 19, FIG. 21, and FIG. 23 show the relationship between the heat treatment temperature (° C.) and the Schottky barrier value ϕB (eV). In FIG. 19, FIG. 21, and FIG. 23, the horizontal axis is the heat treatment temperature (annealing temperature (° C.)); and the vertical axis is the Schottky barrier value (SBH) ϕB (eV). Ti of FIG. 19 shows the experiment results of the cell of the example 1. TiC shows the experiment results of the cell of the example 2. $TiSi_2$ shows the experiment results of the cell of the example 3. Mo of FIG. 21 shows the experiment results of the cell of the example 4. $Mo_2C$ shows the experiment results of the cell of the example 5. W of FIG. 23 shows the experiment results of the cell of the example 6. WC shows the experiment results of the cell of the example 7. $W_2C$ shows the experiment results of the cell of the example 8.

FIG. 20, FIG. 22, and FIG. 24 show the relationship between the heat treatment temperature (° C.) and the n-factor (a.u). In FIG. 20, FIG. 22, and FIG. 24, the horizontal axis is the heat treatment temperature (annealing temperature (° C.)); and the vertical axis is the n-factor.

It can be seen from FIG. 20 that the n-factor was stable at 1.05 or less and the Schottky barrier value ϕB was 0.8 to 1.0 (eV) at 500 to 800° C. for the TiC electrode (the example 2) and the $TiSi_2$ electrode (the example 3).

The n-factor also was in the range of 1.06 to 1.10 and ϕB exceeded 1.0 (eV) at 500 to 600° C. for the Ti electrode (the example 1).

From this result, it can be seen that the Schottky barrier is sufficiently reduced for the TiC electrode and the $TiSi_2$ electrode for which the heat treatment of 800° C. or less was performed. For the TiC electrode for which the 500° C. heat treatment was performed, the Schottky barrier value ϕB was 0.995 (eV); and the effective Richardson constant was 129 (A/cm 2/K 2).

The theoretical value of the effective Richardson constant for 4H—SiC is 146 ($A/cm^2 \cdot K^2$). For the TiC electrode (the example 2), looking at the effective Richardson constant as well, it can be seen that the decrease of the Schottky barrier value and the spreading of the depletion layer are obtained. In other words, it can be said that the depletion layer has spread in a cell having a similar I-V characteristic.

It can be seen from FIG. 21 that comparing the Mo electrode and the $Mo_2C$ electrode, excellent results are obtained for the $Mo_2C$ electrode even for heat treatment at high temperatures. This shows that the $Mo_2C$ electrode reacts with SiC less easily than does Mo electrode. Also, it can be seen from FIG. 22 that the $Mo_2C$ electrode has an n-factor of 1.00. The n-factor approaching 1 shows that a depletion layer near the theoretical value is formed. From this aspect as well, it can be seen that the $Mo_2C$ electrode is superior to the Mo electrode.

In FIG. 23, the $W_2C$ electrode has a slightly better characteristic than the W electrode and the WC electrode. In FIG. 24 as well, it was found that the $W_2C$ electrode has an n-factor of 1.00; and an excellent characteristic is obtained.

Examples 9 to 11

Figure 25:
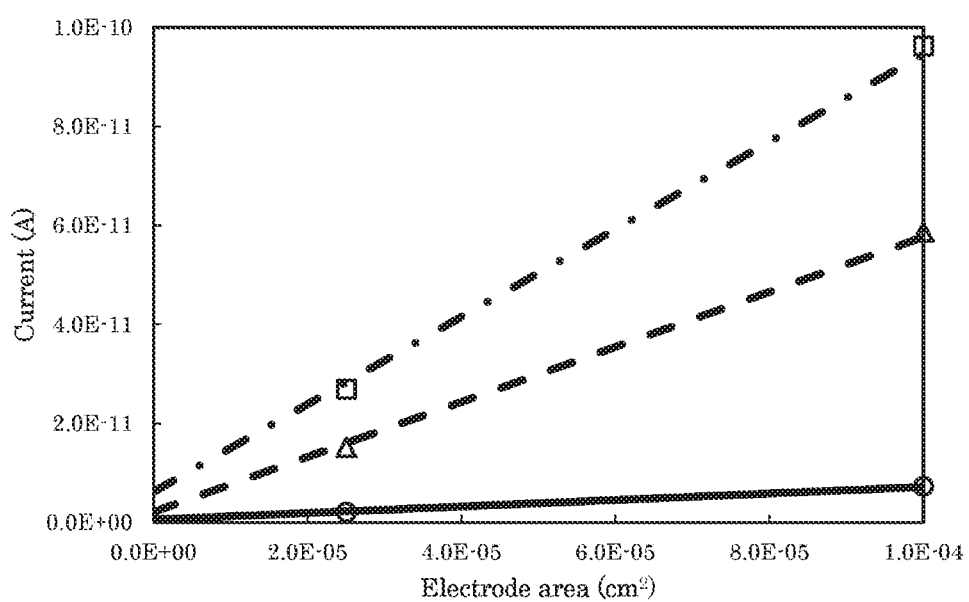
FIG. 25 is a figure showing the relationship of the electrode area and the leakage current of the Schottky-type cell according to the examples.

The leakage current value in the case where the width L of the front-side electrode 3 is changed as in Table 3 was measured for cells having structures similar to those of the examples 1 to 3. For the measurement, the leakage current was measured when −1.0 V was applied after heating in a nitrogen atmosphere at 800° C.×1 minute. The results are shown in a Table 3 and FIG. 25.

TABLE 3

| Electrode material | Leakage current value ($\times 10^{-11}$ A) when front-side electrode size is L × L ($\mu m^2$) | | | |
|---|---|---|---|---|
| | L = 0.8 μm | L = 10 μm | L = 50 μm | L = 100 μm |
| Example 9  Ti | 1.1 | 1.2 | 2.4 | 9.6 |
| Example 10  TiC | 0.4 | 0.6 | 0.8 | 1.1 |
| Example 11  $TiSi_2$ | 0.6 | 0.8 | 1.8 | 6.1 |

Comparing the Ti electrode (the example 9), the TiC electrode (the example 10), and the $TiSi_2$ electrode (the example 11), it was found that the leakage current value is lower for the example 10 and the example 11 than for the example 9. The example 9 and the example 11 show that the leakage current also is reduced by reducing the surface area (the width L) of the electrode. That is, for the Ti electrode and the $TiSi_2$ electrode, it was found that there is a correlation between the electrode area and the leakage current value. On the other hand, the leakage current value was small for TiC regardless of the electrode area. It can be seen that compared to the Ti electrode and the $TiSi_2$ electrode, the leakage current value is small for the TiC electrode.

Examples 12 to 29 and Comparative Example 1

Figure 26:
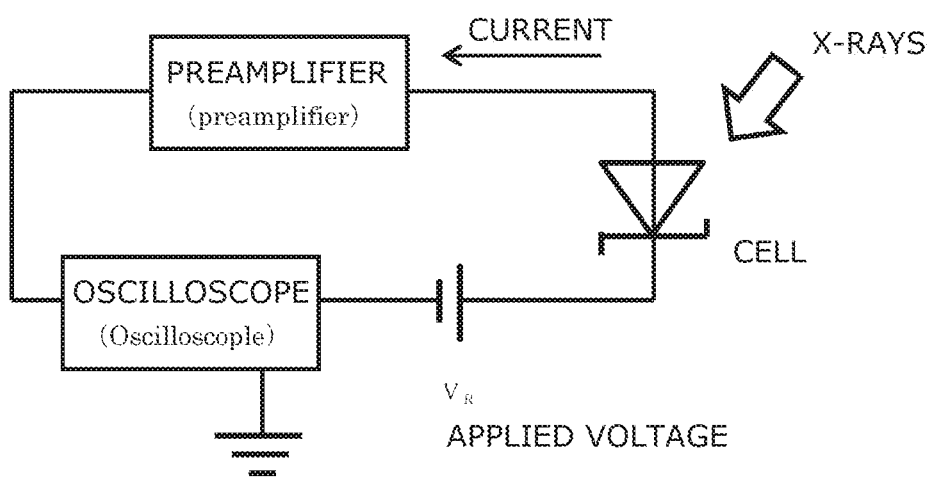
FIG. 26 is a circuit diagram showing a measurement circuit of the photon counting-type radiation detector.

The photon counting-type X-ray detectors shown in Table 4 were made using the cells of the examples 1 to 8. The size of the front-side electrode of each cell is 100 μm×100 μm. A heat treatment process of 500° C. was performed for each example that was used. It was confirmed whether or not each photon counting-type X-ray detector can detect the X-ray photons passing through the screening object. The detection of the X-ray photons was performed by the measurement circuit shown in FIG. 26.

Also, for the measurement conditions, X-rays were irradiated using an X-ray tube; and it was measured whether or not the X-rays can be detected. For the X-ray tube, the tube voltage was unified at 120 kV; and the tube current was set to 300 mA or 100 mA. Under these conditions, the X-rays were irradiated for 2 seconds; and it was confirmed whether or not the X-rays can be detected. The X-ray detector of the examples was implemented using an applied voltage VR of 40 V and 100 V. The results are shown in Table 4. In Table 4, the detector is shown as "possible" when the X-rays passing through the cell are confirmed and the X-rays can be detected. The detector is shown as "impossible" when the X-rays passing through are not confirmed or the X-rays cannot be detected. Also, a cell in which CdTe is used as the X-ray absorption layer was prepared for comparison. The applied voltage was set to 1000 V for the comparative example 1.

TABLE 4

| | | X-ray irradiation conditions (tube voltage 120 kV) | |
| --- | --- | --- | --- |
| Detector | Cell | Tube current 300 mA Possibility of detecting transmitted X-rays | Tube current 100 mA Possibility of detecting transmitted X-rays |
| Example 12 | Cell (single layer) of example 1 | Possible | Possible |
| Example 13 | Cell (single layer) of example 2 | Possible | Possible |
| Example 14 | Cell (single layer) of example 3 | Possible | Possible |
| Example 15 | Cell (single layer) of example 4 | Possible | Possible |
| Example 16 | Cell (single layer) of example 5 | Possible | Possible |
| Example 17 | Cell (single layer) of example 6 | Possible | Possible |
| Example 18 | Cell (single layer) of example 7 | Possible | Possible |
| Example 19 | Cell (single layer) of example 8 | Possible | Possible |
| Example 20 | Cell (2 layers) of example 1 | Possible | Possible |
| Example 21 | Cell (2 layers) of example 2 | Possible | Possible |
| Example 22 | Cell (2 layers) of example 3 | Possible | Possible |
| Example 23 | Cell (3 layers) of example 4 | Possible | Possible |
| Example 24 | Cell (3 layers) of example 5 | Possible | Possible |
| Example 25 | Cell (3 layers) of example 6 | Possible | Possible |
| Example 26 | Cell (5 layers) of example 7 | Possible | Possible |
| Example 27 | Cell (10 layers) of example 8 | Possible | Possible |
| Example 28 | Cell (30 layers) of example 2 | Possible | Possible |
| Example 29 | Cell (50 layers) of example 5 | Possible | Possible |
| Comparative example 1 | Cell (10 layers) of CdTe | Impossible | Impossible |

It can be seen from the table that the detection of the X-ray photons was possible for the photon counting-type X-ray detectors including cells using SiC layers for either a single-layer structure or a stacked structure. In the examples 20 to 29, the X-ray photons were detectable in the cells of each layer. These results show that as a detector, the X-rays are transmitted; and the depletion layer of each cell spreads. Also, the detection current value can be increased by increasing the number of stacks. Therefore, a higher information amount of the X-rays passing through the screening object is obtained in the thickness direction of the detector (an improvement of the time resolution). Therefore, the detection accuracy also can be increased for an X-ray inspection device such as CT, etc.

Also, the comparative example 1 is an example in which 10 layers of CdTe cells are stacked. Although the applied voltage was high and was 1000 V, the X-ray photons could not be detected in the cells of the second and subsequent layers. This is because CdTe does not transmit the X-rays; and the X-rays cannot be detected by the lower layers even when a stacked structure is used. CdTe transmits intense rays such as gamma rays, but does not transmit X-rays easily. Therefore, CdTe is not suited to the detection of X-ray photons.

Although several embodiments of the invention are illustrated hereinabove, these embodiments are presented as examples and are not intended to limit the scope of the invention. These novel embodiments can be implemented in other various forms; and various omissions, substitutions, modifications, etc., can be performed without departing from the spirit of the invention. These embodiments and their modifications are within the scope and spirit of the invention and are within the scope of the invention and equivalents recited in the claims. Also, the embodiments described above can be implemented in combination with each other.

What is claimed is:

1. A photon counting-type radiation detector, comprising:
   a first cell transmitting radiation; and
   a second cell stacked with the first cell, the second cell absorbing the radiation passing through the first cell, wherein
   the first cell and the second cell are of direct photon counting,
   the first cell includes a first front-side electrode, a first backside electrode, and a first epitaxial layer,
   the second cell includes a second front-side electrode, a second backside electrode, and a second epitaxial layer,
   the first front-side electrode, the first backside electrode, the second front-side electrode, and the second backside electrode include nitride or silicide, the nitride or the silicide includes one selected from a group consisting of Ti, W, Mo, Ta, and Nb,
a thickness of the first epitaxial layer and a thickness of the second epitaxial layer are not less than 5 µm and not more than 200 µm,
a width of the first front-side electrode and a width of the second front-side electrode are 250 µm or less.

2. The photon counting-type radiation detector according to claim 1, wherein at least one of the first cell or the second cell includes a SiC layer.

3. The photon counting-type radiation detector according to claim 2, wherein the SiC layer has a multilayer structure.

4. The photon counting-type radiation detector according to claim 1, wherein the first cell and the second cell are of a Schottky type.

5. The photon counting-type radiation detector according to claim 1, further comprising a controller connected to the front-side electrode and the backside electrode of each of the first cell and the second cell.

6. The photon counting-type radiation detector according to claim 5, wherein the controller detects a current flowing between the front-side electrode and the backside electrode of the first cell and a current flowing between the front-side electrode and the backside electrode of the second cell.

7. The photon counting-type radiation detector according to claim 1, wherein at least a portion of the front-side electrode of the first cell opposes, in a travel direction of the radiation, at least a portion of the backside electrode of the first cell.

8. The photon counting-type radiation detector according to claim 1, wherein at least a portion of the backside electrode of the first cell opposes, in a travel direction of the radiation, at least a portion of the front-side electrode of the second cell.

9. A radiological inspection device, comprising the photon counting-type radiation detector according to claim 8 mounted therein.

10. The photon counting-type radiation detector according to claim 1, wherein
the first cell and the second cell are of a Schottky type, and
a width of the front-side electrode of each of the first cell and the second cell is 206 µm or less.

11. A radiological inspection device, comprising the photon counting-type radiation detector according to claim 10 mounted therein.

12. A radiological inspection device, comprising the photon counting-type radiation detector according to claim 1 mounted therein.

13. The radiological inspection device according to claim 12, further comprising a voltage supply configured to apply a voltage between the first front-side electrode and a first backside electrode and to apply a voltage between the second front-side electrode and a second backside electrode of 300 V or less.

14. A radiological inspection device, comprising the photon counting-type radiation detector according to claim 7 mounted therein.

15. The photon counting-type radiation detector according to claim 1, wherein a width of the second backside electrode is longer than a width of the second front-side electrode.

16. The photon counting-type radiation detector according to claim 15, wherein the first backside electrode and the second front-side electrode are provided between the first front-side electrode and the second backside electrode.

17. The photon counting-type radiation detector according to claim 15, wherein the width of the second backside electrode is longer than a width of the first front-side electrode and longer than a width of the first backside electrode.

18. The photon counting-type radiation detector according to claim 15, wherein the second front-side electrode and the second backside electrode are electrically separated from the first front-side electrode and the first backside electrode.

* * * * *